:

US009261885B2

(12) United States Patent
Tryfonos et al.

(10) Patent No.: US 9,261,885 B2
(45) Date of Patent: Feb. 16, 2016

(54) PORTABLE METERED FLOW APPARATUS FOR CALIBRATION/BUMP TESTING

(75) Inventors: Andrew Tryfonos, Morganville, NJ (US); Eric E. Brooking, Newark, DE (US); Robert A. DeNicola, Newark, DE (US); Ryan W. Kauler, Telford, PA (US); Joshua D. Treisner, Wilmington, DE (US); Kayla R. Burnim, Amherst, MA (US); Ryan B. Adelman, Delmar, MD (US)

(73) Assignee: Air Liquide Advanced Technologies U.S. LLC, Houston, TX (US)

( * ) Notice: Subject to any disclaimer, the term of this patent is extended or adjusted under 35 U.S.C. 154(b) by 511 days.

(21) Appl. No.: 13/361,368

(22) Filed: Jan. 30, 2012

(65) Prior Publication Data

US 2012/0125076 A1      May 24, 2012

Related U.S. Application Data

(63) Continuation of application No. 12/199,994, filed on Aug. 28, 2008, now Pat. No. 8,122,753.

(60) Provisional application No. 60/969,179, filed on Aug. 31, 2007.

(51) Int. Cl.
  *G01N 33/00* (2006.01)
  *G05D 16/04* (2006.01)
  *G01N 1/22* (2006.01)

(52) U.S. Cl.
  CPC ............ *G05D 16/04* (2013.01); *G01N 33/0006* (2013.01); *G01N 2001/2276* (2013.01); *Y10T 137/8208* (2015.04)

(58) Field of Classification Search
  CPC ................. G01N 33/0006; G01N 2001/2276; G01N 21/278; G05D 16/04; Y10T 137/8208
  USPC .......... 73/1.05, 1.06, 23.2, 23.3, 23.34, 31.04
  See application file for complete search history.

(56) References Cited

U.S. PATENT DOCUMENTS 3,276,241 A * 10/1966 Hübner .......................... 73/23.2
3,343,402 A *  9/1967 Hubner ........................ 73/31.02
(Continued)

FOREIGN PATENT DOCUMENTS

EP          445927 A2 *  9/1991  ........... G01N 27/417
GB        2369888          12/2002
(Continued)

OTHER PUBLICATIONS

PCT/US2008/074783 Search Report.
(Continued)

*Primary Examiner* — Peter Macchiarolo
*Assistant Examiner* — Natalie Huls
(74) *Attorney, Agent, or Firm* — Elwood L. Haynes; Allen E. White

(57) ABSTRACT

A portable metered flow apparatus for accurately providing calibration gas from a calibration gas source to a gas monitoring instrument in order to permit calibration/bump testing of the instrument comprising a regulator and a gas delivery device that includes a solenoid valve, an electronic timing circuit, means for providing power to the solenoid valve and the electronic timing circuit, a power switch for activating the electronic timing circuit, means for activating the release of calibration gas; and optionally one or more LED lights. A method for calibration/bump testing of a gas monitoring device utilizing the portable metered flow apparatus is also provided.

17 Claims, 9 Drawing Sheets

(56) References Cited

U.S. PATENT DOCUMENTS

| | | | |
|---|---|---|---|
| 3,375,700 A | 4/1968 | Hubner | 73/31.02 |
| 3,948,604 A * | 4/1976 | Hoppesch | 422/84 |
| 6,266,995 B1 | 7/2001 | Scott | |
| 6,520,220 B2 * | 2/2003 | Durkin et al. | 141/94 |
| 7,146,841 B2 | 12/2006 | Forrest | 73/1.06 |
| 7,377,147 B1 * | 5/2008 | Scheffler et al. | 73/1.06 |
| 7,530,255 B2 * | 5/2009 | Frank et al. | 73/1.03 |
| 7,805,974 B2 * | 10/2010 | Scheffler et al. | 73/1.06 |
| 8,539,809 B2 * | 9/2013 | Hemmingsson et al. | 73/1.06 |
| 2004/0074279 A1 * | 4/2004 | Forrest | 73/1.06 |
| 2005/0000981 A1 * | 1/2005 | Peng et al. | 222/3 |
| 2006/0049207 A1 * | 3/2006 | Bogoshian et al. | 222/196 |
| 2006/0081033 A1 * | 4/2006 | Peng | 73/31.05 |
| 2010/0069902 A1 | 3/2010 | Sartor et al. | 606/41 |
| 2011/0107813 A1 * | 5/2011 | Guth et al. | 73/1.06 |
| 2014/0041436 A1 * | 2/2014 | Knott et al. | 73/1.06 |

FOREIGN PATENT DOCUMENTS

| | | |
|---|---|---|
| WO | 9721999 | 6/1997 |
| WO | 2008124213 | 10/2008 |

OTHER PUBLICATIONS

PCT/US2008/074783 International Preliminary Report on Patentability and Written Opinion.

* cited by examiner

PORTABLE METERED FLOW APPARATUS FOR CALIBRATION/BUMP TESTING

CROSS-REFERENCE TO RELATED APPLICATIONS

This application claims priority to U.S. patent application Ser. No. 12/199,994, filed Aug. 28, 2008, which claims the benefit of U.S. Provisional Application No. 60/969,179, filed Aug. 31, 2007.

FIELD OF THE INVENTION

The present invention relates to a portable metered flow apparatus and process for accurately providing calibration gas from a calibration gas source to a gas monitoring instrument in order to permit calibration/bump testing of the gas monitoring instrument. More specifically, the present invention relates to a portable metered flow apparatus for calibration/bump testing of a gas monitoring instrument, a calibration/bump testing process using the same and a calibration system that utilizes the portable metered flow apparatus.

BACKGROUND OF THE INVENTION

Gas monitoring instruments, also known as gas detection units, are used in a wide variety of different fields to detect the presence of a gas in a particular amount. In some instances, the gases being monitored are hazardous in nature so that their presence in a particular area can pose a significant health risk to anyone exposed to the gases. The monitoring of such gases falls within the field of industrial hygiene and includes, for example, monitoring or detection of the accumulation of carbon monoxide in underground parking garages or the accumulation of gases in underground mines, manholes, or other confined spaces. Gas monitoring instruments are also used as breath alcohol analyzers, for example by police forces in order to determine whether or not a person has been drinking and their level of intoxication. In each of these cases, it is important to be able to detect the presence of the gas as well as levels of the gas, including potentially harmful levels. Therefore, it is critical to make certain that the gas monitoring instrument functions properly and gives an accurate reading since failure to provide an accurate reading could result in adverse situations such as a fatality caused by excess exposure to toxic/hazardous gases or injury caused by the inability to confirm whether or not a person has been drinking.

In order to assure that an instrument detects gas levels accurately and reliably, it is necessary to test the instrument with a known concentration of gas. By exposing the instrument to a known concentration of gas, it is possible to determine not only the accuracy of the instrument but also whether the instrument is functioning properly. This testing includes, for example whether specific alarms or indicators are also functioning properly in gas monitoring instruments used in industrial hygiene and the accuracy of the instrument in breathalyzers. This testing is often referred to as "calibration". In addition to calibration, people often utilize what is referred to as a "bump" test for testing the accuracy of an instrument. As used herein the term "bump test" refers to a brief exposure (or bump) of the instrument with a known concentration of gas/gases for the purposes of determining whether or not the instrument is functioning properly.

It is also necessary to calibrate/bump test instruments to rule out situations that involve false negatives. For example, when an instrument has lost its sensitivity to a target gas, it may give a reading of zero which would be the same reading that would be given in the absence of any gas. Accordingly, a large number of industries now recommend more frequent calibration/bump testing of instruments.

Original equipment manufacturers (OEM's) often manufacture instruments that can regulate or meter gas flow. While these instruments do require a regulator, a regulator is typically an accessory to the system. These instruments are also limited to calibrating the OEM's own devices. In addition, the instruments are bulky and therefore not portable. In most cases, they are operated by proprietary software and powered via an AC cord. In the industrial hygiene market, expensive automatic calibration stations and or bump test stations are often used. These are instruments that are peripheral to the regulator and cylinder package and are usually computer controlled. They are also not portable and require proprietary software to dispense the calibration gas.

There are also a variety of additional apparatus on the market which provide calibration/bump testing abilities. However, these apparatus are also very bulky and cumbersome. As a result, they are very difficult, if not impossible, to transport in the field and as a result must be mounted at a stationary station. As used herein, the phrase "in the field" refers to the main area where the gas monitoring instruments are used. For example, "in the field" would refer to "in mines" for gas monitoring instruments used to detect toxic/hazardous gases in mines while "in the field" would refer to "in police vehicles" for gas monitoring instruments used to detect breath alcohol levels. The result is that any instrument needing calibration/bump testing must be brought to this stationary station (to the calibration/bump testing apparatus) rather than having the apparatus be available at the site where the instrument is located or at the site where the instrument is used. As a result, these encumbrances place a limit on the degree of calibration/bump testing that can be conducted since it is necessary to bring the gas monitoring devices to the calibration apparatus rather than carry the calibration apparatus to the people in the field.

In addition, with regard to the prior art apparatus that are currently on the market in the form of stationary stations, there is a high degree of human involvement with regard to these calibration/bump testing apparatus. In many instances, for example, in the field of breath alcohol testing, mechanical preset flow regulators are used to calibrate the portable breathalyzer devices (also commonly referred to as breath alcohol instruments). These regulators all have mechanically controlled mechanical activation buttons or knobs (hand trigger release devices) which have to be pushed and/or held down for a prescribed period of time in order to allow the gas to flow from the calibration gas source to the instrument that is to be calibrated (the gas monitoring instrument). The person using the device must begin counting the predetermined seconds set forth by the manufacturer while holding down the button in order to calibrate/bump test the device. For example, if seven seconds are required for the calibration/bump testing, then the user must push in the button and hold it while they count to seven seconds. During this period of time in which the activation button or knob is pushed in, the valve is opened and gas will flow into the instrument at a given flow rate to approximately the desired volume (flow rate plus time used to dispense a particular volume of gas) before the valve is manually closed. Due to inaccuracy on the operator's part, the result could be the operator holding down the button for less than the necessary time, thereby leading to an insufficient volume of calibration gas being passed to the instrument to be calibrated, or holding down the button for too long thereby leading to an excess amount of calibration gas being passed to the instrument to be calibrated. As is evident, there is great room for human error using such an apparatus.

An unpublished study examining the use of hand trigger release devices showed a 30% error existed between people counting to two seconds and an 20% error existed between people counting to six seconds. In many instances such an error would be considered sufficient to call into question the accuracy of the results obtained especially when considered in cases involving the use of breath alcohol analyzers. In addition to the question of accuracy, often the operator is not getting the maximum cycles from the calibration gas source due to the human error on the part of the operator. In other words, the calibration gas is being wasted.

As a result, there exists a need for an apparatus that can be used in the field for calibration/bump testing of a gas monitoring instrument which overcomes the above noted problems. More specifically, there exists a need for an apparatus for calibration/bump testing that is portable, easy to use, and economical. There also exists a need for a portable apparatus that eliminates the human error associated with calibration/bump testing, thereby resulting in a more reliable and accurate readings for gas monitoring instruments.

In view of the above, it is the objective of the present invention to provide a portable, easy to use, economical, reliable and accurate apparatus and process for calibration/bump testing of a gas monitoring instrument by precisely and accurately dispensing a specific volume of a known calibration gas from a calibration gas source.

SUMMARY

The present invention relates to a portable metered flow apparatus for accurately providing calibration gas from a calibration gas source to a gas monitoring instrument in order to permit calibration and/or bump testing of the gas monitoring instrument and a process for calibrating and/or bump testing in the areas of industrial hygiene and breath alcohol analysis utilizing this apparatus. The portable apparatus comprises a regulator and a gas delivery device that comprises a case that includes a solenoid valve, an electronic timing circuit, a power switch for activating the electronic timing circuit and a means for activating the release of calibration gas. The apparatus further comprises a means for providing power to the electronic timing circuit and the solenoid valve. The present invention further relates to a calibration system which includes a calibration gas source and the portable metered flow apparatus of the present invention.

DETAILED DESCRIPTION OF THE INVENTION

Figure 1:
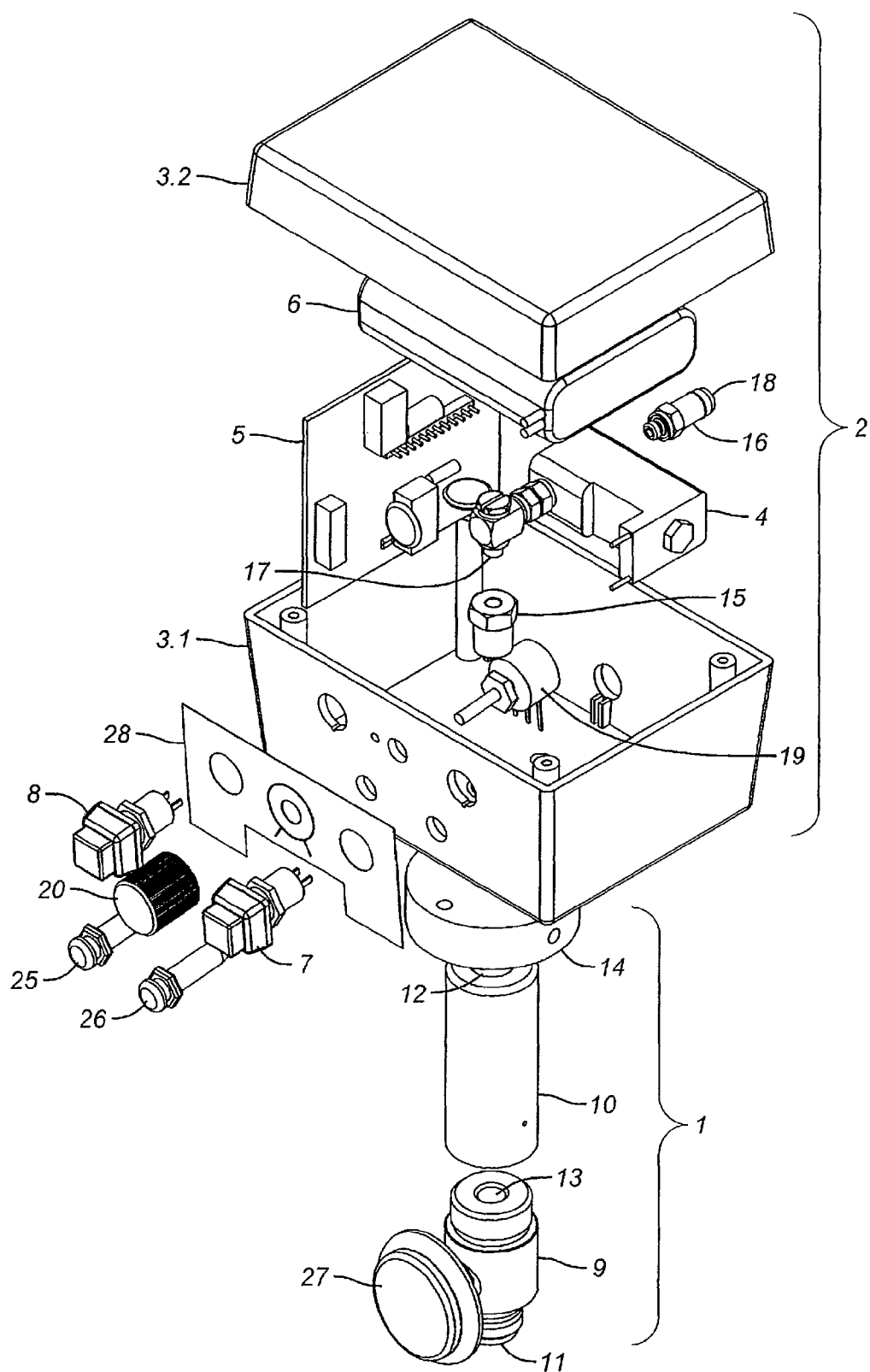
FIG. 1 provides a full depiction of one embodiment of the metered flow apparatus of the present invention that includes a regulator and a box shaped gas delivery device.

The metered flow apparatus of the present invention provides an accurate, light weight, and portable means for transferring calibration gas from a calibration gas source to a gas monitoring instrument to be calibrated. As used throughout the specification with regard to the present invention, the phrase "portable metered flow apparatus" and "metered flow apparatus" are considered to be equivalent unless specified otherwise. The metered flow apparatus of the present invention makes it possible to provide an operator with an accurate, compact tool for calibration/bump testing that can readily be utilized in the field compared to the prior art apparatus which are less accurate (include a manually operated trigger release device attached to the regulator) and due to size and bulkiness require them to be located in stationary bases. As a result, when using the prior art apparatus, the gas monitoring instrument must be brought to the stationary base in order to be calibrated/bump tested (the size and bulkiness of the stationary bases make transport of the prior art apparatus extremely inconvenient, if not impossible, from a logistical standpoint).

The metered flow apparatus of the present invention overcomes the inaccuracies found with regard to dispensing calibration gas with the prior art apparatus since the present apparatus provides a predetermined volume of gas (predetermined volume based on the time of gas release and the rate of gas flow—liters per minute) when the operator activates the release of the calibration gas. After the predetermined volume of gas has been dispensed, the metered flow apparatus automatically shuts off the dispensing of calibration gas. Consequently, the metered flow apparatus of the present invention eliminates calibration gas waste commonly caused by operator error during the calibration/bump testing by providing a more accurate means for dispensing the gas.

The current metered flow apparatus not only significantly decreases operator error by providing a preset or selected volume (amount) of gas from a calibration gas source to the gas monitoring instrument, it also provides an apparatus that can readily be transported in the field by an operator, thereby allowing for easy calibration/bump testing of a gas monitoring instrument in the field. Taking the portable metered flow apparatus to the field makes it possible to calibrate/bump test a gas monitoring instrument on a regular basis, if not prior to every use, without the inconvenience typically associated with calibration/bump testing at a stationary base. This, in turn, assures the operator of a reliable reading of the gas monitoring apparatus.

The metered flow apparatus of the present invention is a compact unit that includes a regulator in fluid connection with a gas delivery device. The gas delivery device comprises a solenoid valve and an electronic timing circuit that controls the timing mechanism. The solenoid valve and electronic timing circuit are contained in a small, compact case that is attached to the regulator. In addition to the solenoid valve and electronic timing circuit, other components that are present in the gas delivery device include a power source, a power switch and a means for activating the release of calibration gas. In alternative embodiments, one or more of these components may be located on the outside of the case and be connected to the internal components via an opening or aperture in the case. The calibration gas is not meant to be a limiting factor with regard to the present invention and may comprise any calibration gas composition that is known for calibration/bump testing. In addition, the structure of the calibration gas source is also not meant to be limiting with regard to the present invention and can be any cylinder or any other appropriate source for storing and supplying calibration gas provided that the cylinder or other appropriate source is portable. In the preferred embodiment of the present invention, the metered flow apparatus is utilized with small refillable or non-refillable cylinders thereby further adding to the ease of transport in the field.

Figure 5:
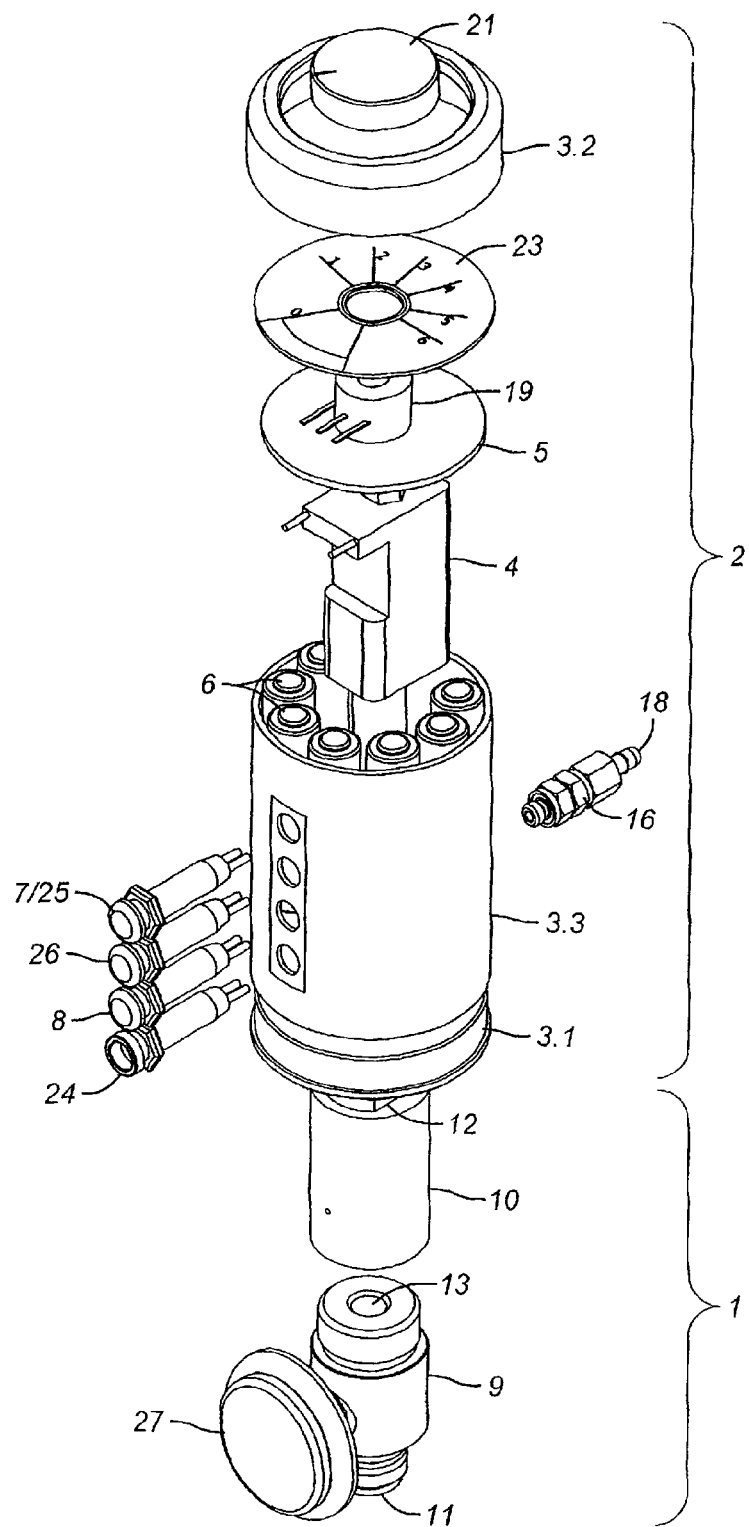
FIG. 5 provides a full depiction of a third embodiment of the metered flow apparatus of the present invention that contains a regulator and a cylindrical gas delivery device.
Figure 9:
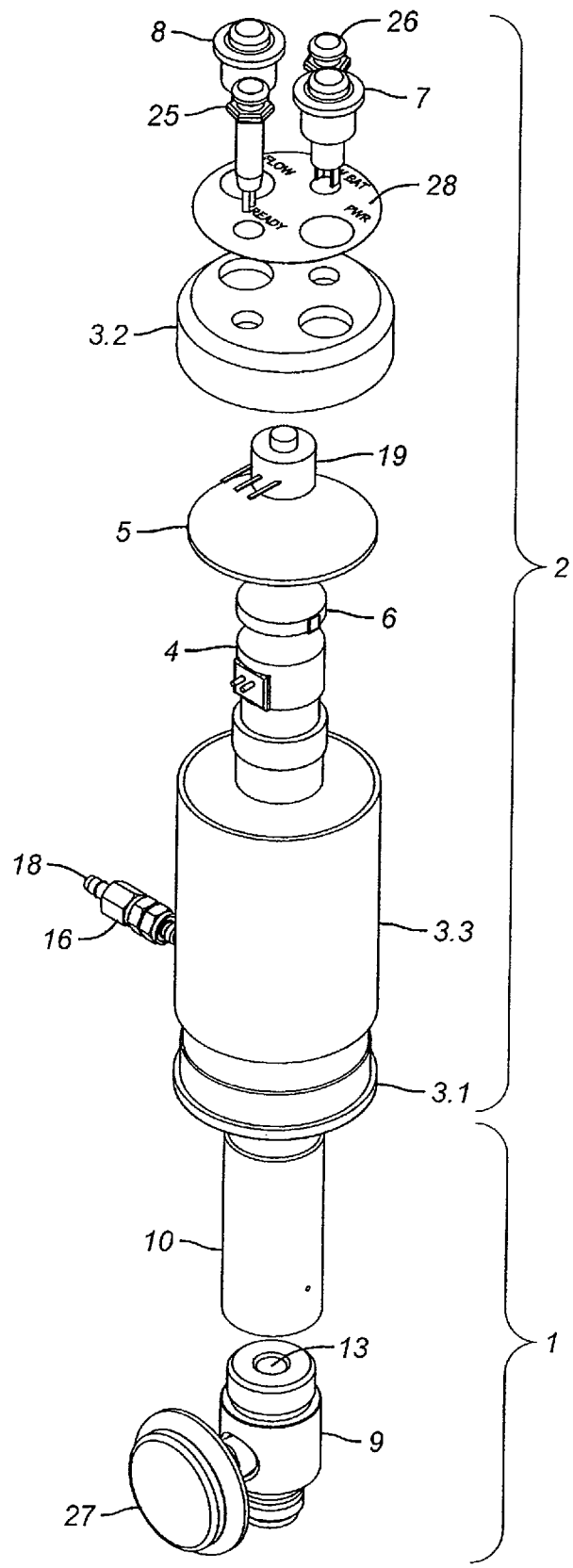
FIG. 9 provides a full depiction of an alternative embodiment of the metered flow apparatus of FIG. 5.

For a further understanding of the nature and objects for the present invention, reference is made to the detailed description, taken in conjunction with the accompanying figures, in which like elements are given the same or analogous reference numbers. Exemplary embodiments of a metered flow apparatus that implements the features of the present invention are depicted in FIGS. 1 to 9, with particular detail being set forth in the embodiments represented by FIGS. 1, 5 and 9. The present metered flow apparatus is designed to connect a source of calibration gas (not shown) with an instrument to be calibrated (also not shown) and to control the flow and volume of calibration gas to the instrument to be calibrated. The metered flow apparatus of the present invention basically comprises two main parts: a regulator (1) whose function is to reduce the gas pressure from the calibration gas source to a desired level and a gas delivery device (2) which controls the time for gas release and the consequently the volume (amount) of calibration gas to be released. The regulator (1) is attached, either directly as shown in FIGS. 5 and 9 or indirectly as shown in FIG. 1, to the gas delivery device (2). As further depicted in FIGS. 1, 5 and 9, the gas delivery device (2) includes a case (3) that contains a solenoid valve (4) and an electronic timing circuit (5), means for providing power (6) to the electronic timing circuit (5) and solenoid valve (4), a power switch (7) for activating the electronic timing circuit (5), and means for activating the release of calibration gas (8). As shown in FIG. 1, the case (3) comprises a top (3.2) and a bottom (3.1) which are shaped to form a hollow rectangular box to allow for the enclosure and protection of the noted components. In alternative embodiments as shown in FIGS. 5 and 9, the case (3) is in the form of a hollow cylinder comprising a cylinder top (3.2), a cylinder bottom (3.1) and a cylinder middle (3.3) joined together and shaped in such a manner to allow for enclosure of the noted components.

The regulator (1) utilized in the present apparatus can be any regulator which functions to reduce gas pressure from one source to another source. Accordingly, the regulators of the present invention may include, but are not limited to, regulators which function to reduce or regulate gas pressure from one source to another source using any variety of means to regulate pressure. These regulators may be of the single stage design (reduce pressure in one step) or the two stage design (actually two regulators housed in one body), with the single stage design being preferred. Such regulators are known in the art and are readily available from a variety of commercial sources such as Ceodeux, Victor and Tescom.

While a variety of different regulators can be used in the present metered flow apparatus, one embodiment of the present invention is shown in FIG. 1. In this embodiment, the regulator (1) has two opposing ends and comprises a regulator body (9) that is connected to a regulator bonnet (10). The regulator includes a regulator inlet (11) located at one end of the regulator (1) (the end of the regulator body (9) that is not connected to the regulator bonnet (10)). This regulator inlet (11) allows for entry of the calibration gas at the same pressure as in the calibration gas cylinder or vessel (which varies as the gas is depleted in the cylinder or vessel) and also for connection of the regulator (1) of the metered flow apparatus to a calibration gas cylinder or vessel in a fluid tight sealing arrangement. In addition, the other end of the regulator (1) (the end of the bonnet (10) that is not connected to the regulator body (9)) includes a regulator outlet (12) that allows for the exit of the calibration gas at a reduced pressure from the regulator (1) and also for connection of the regulator (1) to the gas delivery device (2). The regulator (1) further includes a hollow passageway (13) that extends axially through the regulator inlet (11), regulator body (9), regulator bonnet (10) and regulator outlet (12). A means for regulating pressure (not shown) is seated in the hollow passageway (13) between the regulator inlet (11) and regulator outlet (12). The hollow passageway (13) provides for the passage of the calibration gas into the regulator body (9) through the regulator inlet (11), through the hollow passageway (13) and means for regulating pressure and out of the regulator (1) through the regulator outlet (12). The calibration gas that exits through the regulator outlet (12) is then passed to the solenoid valve (4) via the connection between the regulator (1) and the solenoid valve (4).

As noted, the regulator (1) includes a means to regulate pressure (not shown) positioned within the continuous hollow passageway (13) of the regulator (1) in order to regulate (reduce) the pressure of the calibration gas from the calibration gas source that enters the regulator (1) through the regulator inlet (11). Since the calibration gas is typically stored at a much higher level of pressure than desired for injecting the calibration gas into the gas delivery device (2), means to regulate the pressure to the desired level are utilized. The pressure of the gas in the calibration gas source can be in the order of up to 2200 psi. After passing through the regulator (1), the pressure will in most instances be reduced to a level in the order of about 15 to about 70 psi, preferably from about 30 to about 50 psi, although lower or higher pressures, while typically being less desirable, are also contemplated to be within the scope of the present invention. Such means for regulating the pressure are known in the art and include, but are not limited to, pressure reducing valves, diaphragms, pistons and any other means that function to accomplish the regulation or reduction of pressure from one source to another (in the present case from the calibration gas source to the gas delivery device (2)). By utilizing means such as those noted, it is possible to regulate the pressure of the calibration gas to the desired level prior to the calibration gas being passed from the regulator (1) to the gas delivery device (2). Once the calibration gas enters the regulator inlet (11) of the regulator (1), the calibration gas will come in to contact with the means for regulating pressure. As the calibration gas passes through the means for regulating pressure, the means functions to reduce the pressure of the calibration gas to the more acceptable limit.

The regulator body (9) of the regulator (1) allows for connection of the regulator (1) to the calibration gas source (not shown) while the bonnet (10) of the regulator (1) allows for connection of the regulator (1) to the solenoid valve (4). Therefore, the regulator (1) of the metered flow apparatus further includes a means for attaching one end of the regulator (1) to the calibration gas source and a means for attaching the other end of the regulator (1) to the gas delivery device (2) via the solenoid valve (4).

While the regulator (1) may be attached to the calibration gas source by any means known in the art, preferably the regulator body (9) of the regulator (1) will be threaded to the calibration gas source. In a preferred embodiment, the regulator inlet (11) which is a part of the regulator body (9) includes an externally or male threaded section that connects with a corresponding female threaded outlet port of the calibration gas cylinder or vessel to facilitate transfer of the calibration gas from the cylinder or vessel into the regulator (1). The regulator inlet (11) can include any suitable sealing members, such as elastomeric O-rings, to ensure a fluid tight connection is established and maintained between the regulator (1) device and the cylinder or vessel during operation of the apparatus of the present invention. In instances where the threads do not readily match, it is possible to utilize an adapting piece (not shown) which will allow a sealed connection between the calibration gas source and the regulator (1) thereby allowing for the safe passage of calibration gas from the calibration gas source to the regulator (1).

In addition, as noted before, the opposing end of the regulator (1) is attached to the gas delivery device (2) either directly or indirectly. When the connection is a direct connection as shown in FIGS. 5 and 9, the bonnet (10) of the regulator (1) will be connected to the solenoid valve (4) by any direct means known in the art, such as the use of internal or external threads located in the regulator outlet (12) with corresponding threads in/on the solenoid valve (4) (similar in nature to those described above with regard to the connection of the regulator (1) to the calibration gas source cylinder or vessel). When the connection is indirect, the means of connection may also be any indirect connection means known in the art, such as through the use of an optional clamp (14) and/or one or more adaptors (15). The optional clamp (14) and/or one or more adaptors (15) for connecting the bonnet (10) of the regulator (1) to the gas delivery device (2) are clearly shown in FIG. 1. As noted above, in one embodiment of the present invention, the calibration gas flows through the continuous hollow passageway (13) of the regulator (1) and exits the regulator (1) through the regulator outlet (12) where it then flows into the gas delivery device (2). In certain embodiments, a clamp (14) will be used to connect the regulator (1) to the gas delivery device (2). In other embodiments, a clamp (14) and/or one or more adaptors (15) will be utilized. When one or more adaptors (15) are present, this adaptor(s) (15) will also include a passage which will further allow the calibration gas passing from the regulator (1) to flow through the adaptor (15) and into the solenoid valve/solenoid valve (4) which is disposed within the gas delivery device (2). While the means of connection is not critical, the means must be such to allow for the secure passage of the calibration gas from one component to the other component (from the regulator (1) to the gas delivery device (2)). Accordingly, regardless of the means of connection utilized (direct or indirect), the means will in many instances include one or more suitable sealing members, such as elastomeric O-rings, to ensure a fluid tight connection is established and maintained between the regulator (1) device and the solenoid valve (4) of the gas delivery device (2) of the present invention.

The regulator (1) utilized in the metered flow apparatus of the present invention may also include one or more gauges (27) for indicating pressure levels which are connected to the regulator (1). In embodiments that include one stage regulators, typically one gauge (27) will be present and will measure the pressure of the calibration gas entering the regulator (1). In those embodiments that comprise two stage regulators, two gauges (27) are typically present with one gauge (27) measuring the pressure of the calibration gas entering the regulator (1) and the second gauge (27) measuring the pressure of the calibration gas leaving the regulator (1). Each of these gauges (27) provides a visual display of the amount of pressure.

Unless described otherwise herein, the regulator body (9) and bonnet (10), as well as various other components of the regulator (1), can be constructed of any suitable materials including, without limitation, metals (e.g., stainless steel) and alloys thereof (e.g., brass) and hard or soft plastic and/or polymer materials (e.g., polytetrafluoroethylene, elastomeric materials such as rubber, etc.).

In addition to the regulator (1), the metered flow apparatus of the present invention further includes a gas delivery device (2). As shown in FIGS. 1, 5 and 9, the gas delivery device (2) comprises a case (3) that encloses at least an electronic timing circuit (5) and a solenoid valve (4) and includes a case inlet (not shown but located at the point of attachment of the regulator (1) to the gas delivery device (2)) and a case outlet (not directly shown but depicted at the point where the barb (16) attaches to the solenoid valve (4), the barb (16) passing through this outlet of the case (3)).

The case (3) utilized may be of any shape, including but not limited to a square box (not shown), a rectangular box (see FIGS. 1 to 4), a cylinder (see FIGS. 5 to 9) or a round globe (not shown). In one preferred embodiment of the present invention, as shown in FIG. 1, the case (1) will be in the form of a rectangular box having a case top (3.2) which fits together with a case bottom (3.1) to form the hollow box. In another preferred embodiment, the case (3) will be in the form of a hollow cylinder as shown in FIGS. 5 and 9 having a case top (3.2), a case bottom (3.1) and a case middle (3.3) fit together to form the hollow cylinder. In each embodiment, the case (3) can be configured to allow for the operator to open the case (3) (for example, to change or recharge the batteries (6) or to adjust the time for gas to be dispensed). In still other embodiments, the case (3) will be sealed so that it will be impossible for the operator to open the case (3) (for embodiments where the time of gas delivery cannot be adjusted, or embodiments where the means for changing the time is positioned on the outside of the case (3), or embodiments where the power source (6) is located on the outside of the case (3), or embodiments where rechargeable batteries (6) are used and a port (24) to recharge the batteries extends from the inside to the outside of the case (3)). Also, the shape of the case (3) is not necessarily critical to the invention provided that the case (3) is constructed of a durable material which will withstand the amount of handing associated with being utilized in the field. The case (3) therefore should be constructed of a durable material such as plastic, brass, stainless steel or aluminum. In one preferred embodiment of the present invention, the case (3) is a box or cylinder constructed of a durable plastic. In another alternative embodiment of the present invention, the case (3) is a box or cylinder constructed of brass or aluminum.

Figure 2:
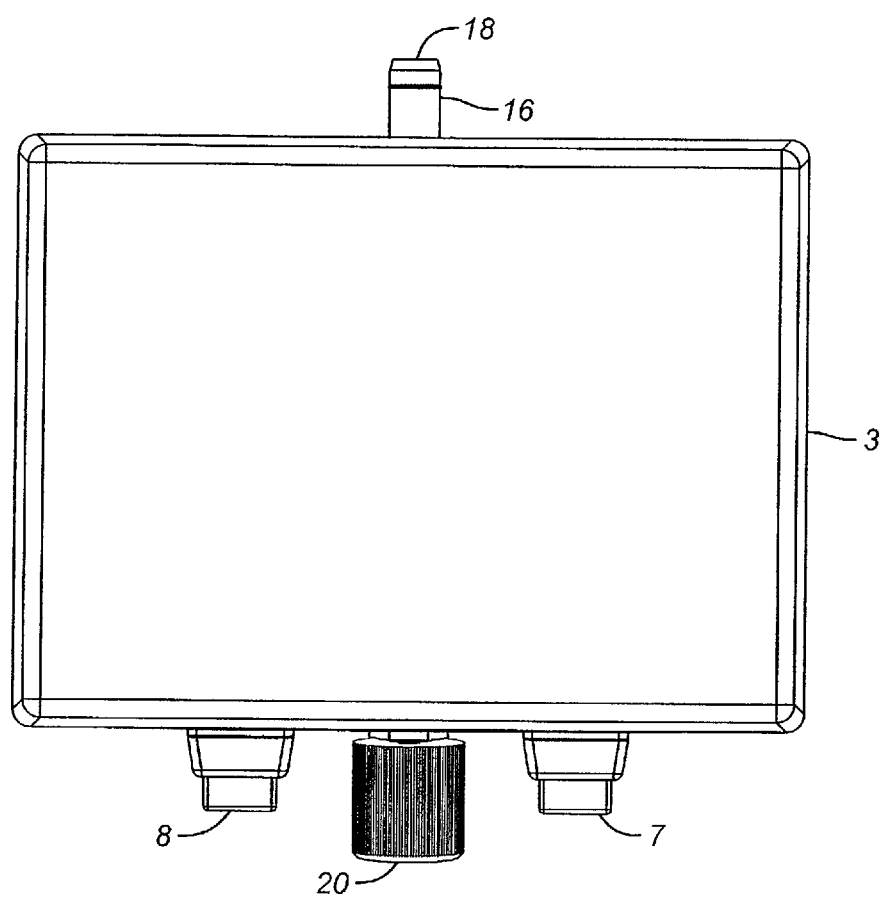
FIG. 2 provides a top view of the gas delivery device of FIG. 1.
Figure 3:
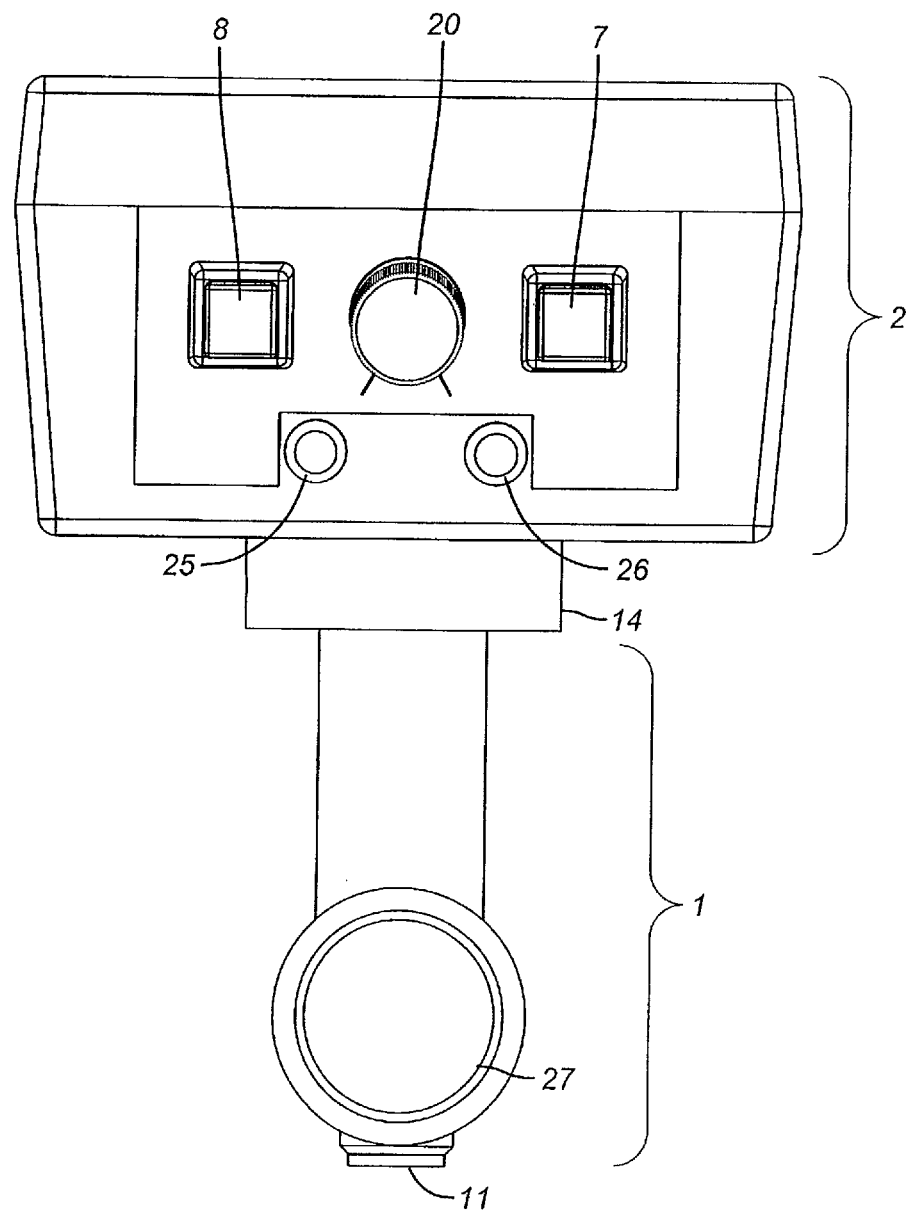
FIG. 3 provides a front view of the metered flow apparatus of FIG. 1.
Figure 4:
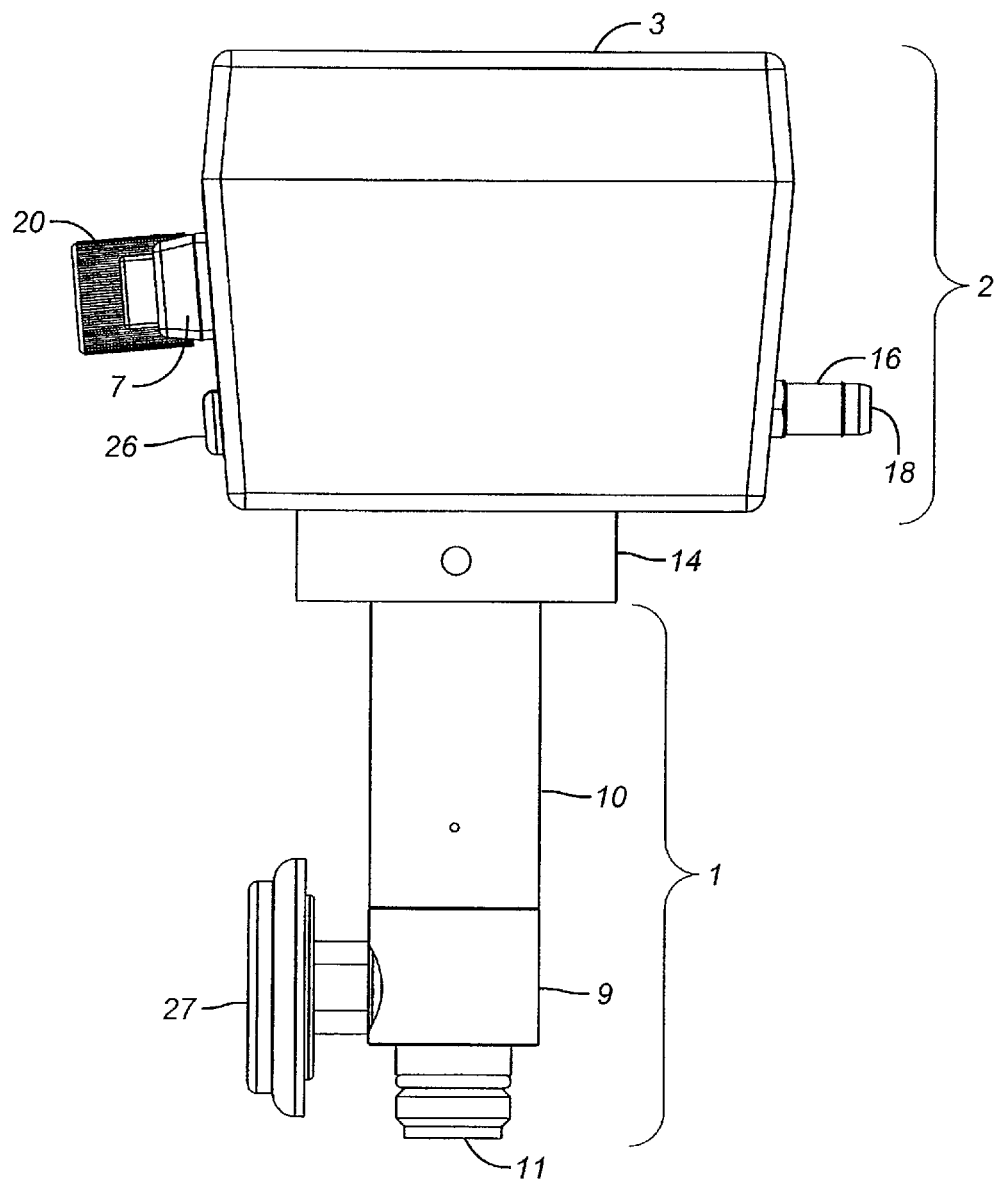
FIG. 4 provides a side view of the metered flow apparatus of FIG. 1.
Figure 6:
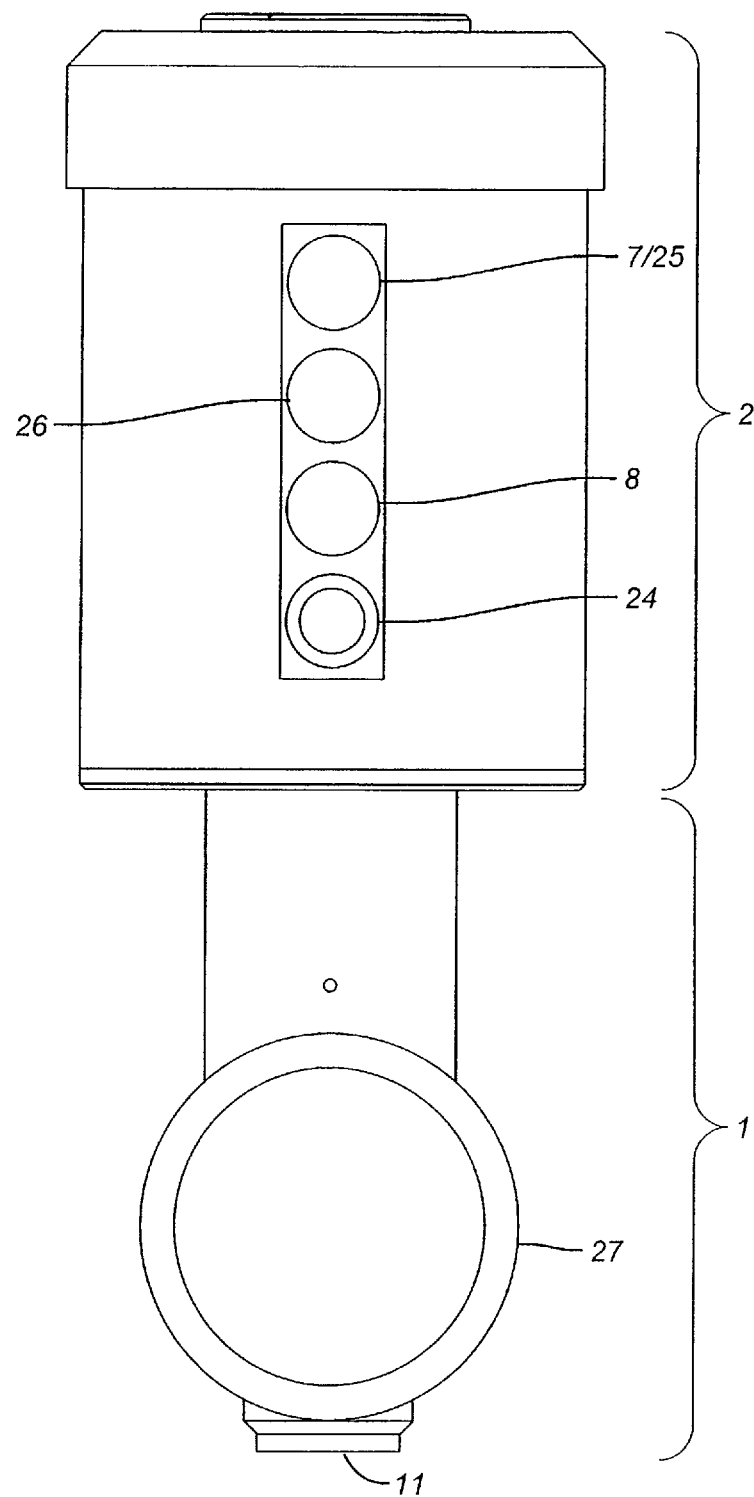
FIG. 6 provides a front view of the gas delivery device of FIG. 5.
Figure 7:
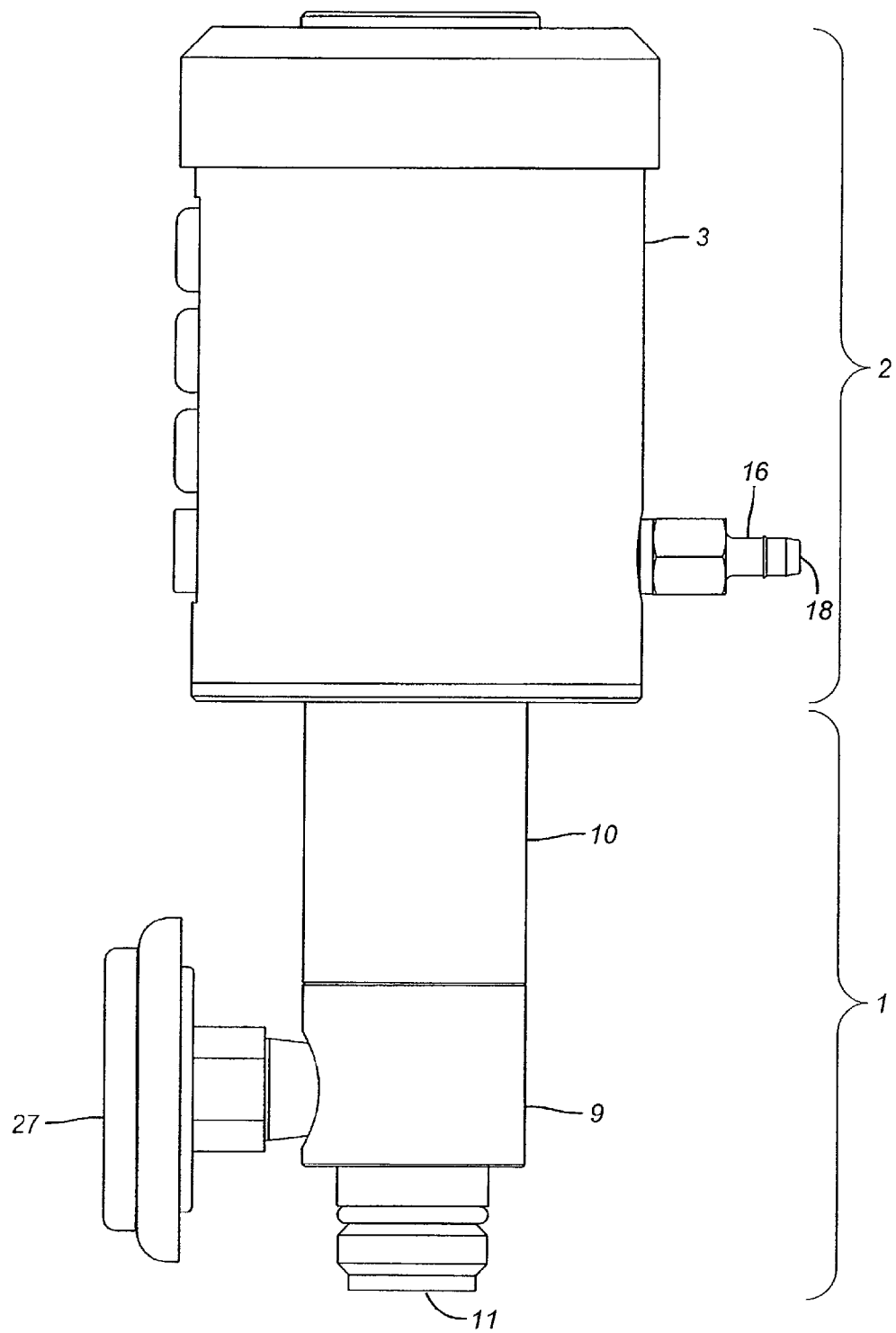
FIG. 7 provides a side view of the metered flow apparatus of FIG. 5.
Figure 8:
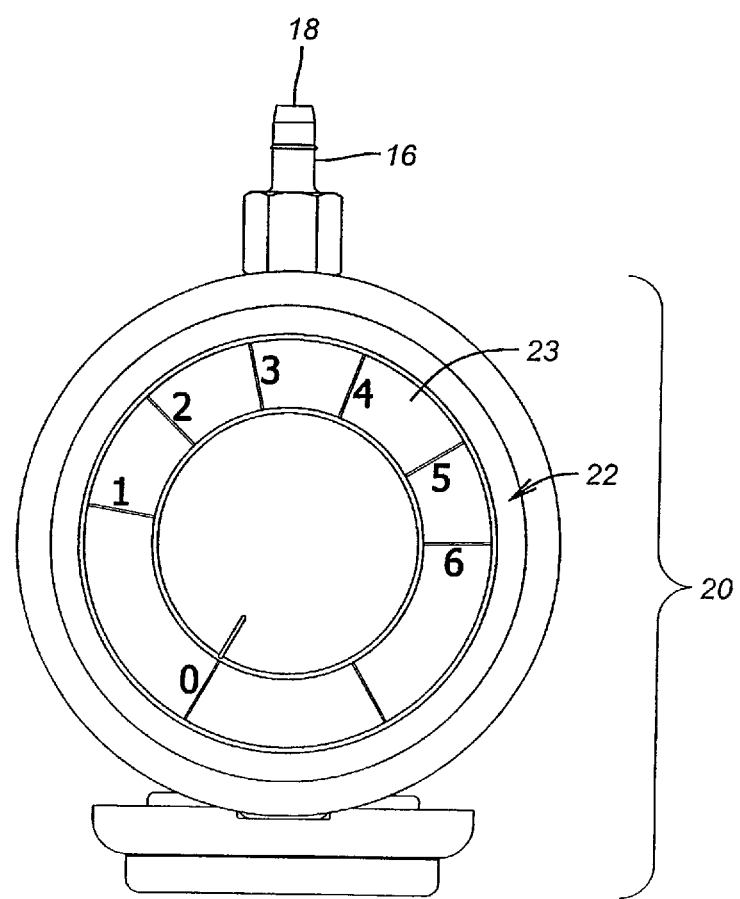
FIG. 8 provides a top view of the metered flow apparatus of FIG. 5.

One critical aspect of the present invention is the combined size of the gas delivery device (2) and regulator (1). This is very important to the invention since one of the main objectives of the present invention is to provide an apparatus that is readily portable in the field and can be easily used by a single operator. More specifically, one objective of the present invention is to have an apparatus which can be held in one hand while being operated by a single operator in the field. In order to do this, the combined size of the gas delivery device (2) and regulator (1) should be such that the outer measurements of the apparatus (the regulator (1) joined to the gas delivery device (2)) are equal to or less than about 7 inches length×about 6 inches width×about 6 inches depth, preferably equal to or less than about 4.5 inches length×about 4.5 inches width×about 4.5 inches depth. In one preferred embodiment of the present invention as shown in FIGS. 2 and 3 which depict the top and front views respectively of the portable metered flow apparatus, the outer case (3) of the gas delivery device (2) is a box of a size such that when combined with the regulator (1) the entire metered flow apparatus has outer measurements in which the length of the apparatus (measured from the top of the apparatus to the bottom of the apparatus) is about 6.0 inches or less, the width of the apparatus (measured across the front face of the apparatus from the widest point on front face directly across to the point opposite but within the same plane that is the widest point) is about 4.5 inches or less and the depth of the apparatus (measured from the point on the front face that protrudes forward to the opposite point on the back face that protrudes back the most as shown in FIG. 2) is about 4.5 inches or less. In another preferred embodiment, the measurements range from about 6.0 inches length×about 6.0 inches width×about 6.0 inches depth. In still another embodiment of the present invention as shown in FIGS. 6 and 7, the outer case (3) of the gas delivery device (2) is a cylinder of a size such that the metered flow apparatus has measurements wherein the length of the of the apparatus (measured from the end of the regulator (1) to the end of the gas delivery device (2)) is about 7.0 inches or less, the width of the apparatus (measured across the broadest portion of the cylinder) is about 4.0 inches or less and the depth of the apparatus (measured from the point on the front face that protrudes forward the most to the distance opposite on the back face that depicts the point that protrudes back the most) is about 4.0 inches or less. In a preferred embodiment, the measurements for the cylinder will be about 6.0 inches length×about 3.0 inches width×about 3.0 inches depth, even more preferably about 6.0 inches length×about 2.0 inches width×about 2.9 inches depth. Accordingly, typical regulators (1) envisioned for use in the present invention are those having proportions that would allow the apparatus of the present invention to meet the size proportions noted above regardless of the shape of the gas delivery device (2).

The solenoid valve (4) of the present invention includes an entrance for calibration gas (17) and an exit for calibration gas (not shown). The entrance for calibration gas (17) allows for connection of the solenoid valve (4) to regulator (1) (or the bonnet (10) of the regulator (1)) either directly or indirectly as discussed hereinbefore. Whether the connection is direct or indirect will likely depend upon the configuration of the various components utilized in the present invention. While some solenoid valves (4) may be readily equipped to attach directly to a regulator (1) as depicted in FIGS. 5 and 9, in some cases such as that shown in FIG. 1 it may be necessary to provide a one or more further components to adapt the solenoid valve (4) for attachment to the regulator (1) as discussed hereinbefore. In these cases, the means which would allow connection could be an elbow (29) or an elbow (29) in combination with one or more adaptors (15). Those of ordinary skill in the art will recognize that a "solenoid valve in combination with one or more elbows and/or adaptors" is often referred to as a "solenoid valve assembly". Accordingly, the present invention is meant to cover both solenoid valves and solenoid valves in combination with multiple elbows and/or adaptors—solenoid valve assemblies. When an elbow (29) in combination with one or more adaptors (15) is used, one end of the elbow (29) will be threaded into the center of an adaptor (15) or bonnet (10) and the other end will be threaded into the entrance for calibration gas (17) of the solenoid valve (4). The embodiment depicted in FIG. 1 provides for the use of an elbow (29) in conjunction with two adaptors (15). In this particular embodiment, the entrance for calibration gas (17) is depicted going into the elbow and attached adaptor before going into the solenoid valve. Calibration gas being passed from the regulator will therefore enter and flow through the elbow (29) and adaptor (15) before entering the solenoid valve (4).

The exit for calibration gas allows for connection of the solenoid valve (4) to the gas monitoring instrument (not shown) to be calibrated. In many instances, devices such as a threaded adapter, a rubber or plastic tip or a barb (16) of the type that are commonly used on prior art regulators for connection to instruments to be calibrated will be utilized to connect the exit for calibration gas of the solenoid valve (4) to the instrument to be calibrated. In the embodiments depicted in the various figures, the device depicted is a barb (16). When such a barb (16) is utilized, it will commonly be of the type that will allow threaded joining of one end of the barb (16) to the solenoid valve in the same manner as described hereinbefore with regard to the attachment of the regulator to the calibration gas cylinder/vessel. The other end of the barb (16) would connect either directly to the instrument to be calibrated using known means or would be connected to the instrument to be calibrated via a tube, hose or pipe. The calibration gas exiting the solenoid valve (4) passes through the barb (16) and exits via the barb exit (18). The barb (16) utilized may be of any type of durable material such as stainless steel or brass although other materials may also be used.

As noted above, the solenoid valve (4) allows for the passage of calibration gas when the valve is opened. In one embodiment of the present invention, the solenoid valve can handle a maximum flow rate of up to about 20.00 liters per minute of gas, in other instances up to about 16.00 liters per minute of gas and in still other embodiments, up to about 6.00 liters per minute of gas flow. Generally, the flow rate of the gas will be about 6.00 liters per minute or less with the average flow rate being on the order of about 0.05 to about 6.00 liters per minute, preferably about 0.50 to about 4.00 liters per minute, and even more preferably about 0.50 to about 2.00 liters per minute. In addition, preferably the solenoid valve (4) will have a temperature range from about −15° C. to about 50° C. (about 5° F. to about 122° C.), even more preferably from about 10° C. to about 27° C. (about 50° F. to about 80° C.). Solenoid valves of the type described are known in the art and are readily available. Such valves are commercially available from companies such as Coast Pneumatics, Clippard and SMC. While the size of the solenoid valve (4) may vary, it must be such that it easily fits inside of the gas delivery device case (3) utilized along with the other components.

The solenoid valve may also be made of any material that is durable. For example, the housing can be hard, durable plastic, brass, stainless steel or aluminum. In many instances, the housing will comprise hard durable plastic.

The electronic timing circuit (5) of the present invention is also fitted to be included in the case (3) of the gas delivery device (2). The electronic timing circuit (5) is included in order to activate the solenoid valve (4) for the purpose of opening and closing the valve. The electronic timing circuit (5) is connected to the solenoid valve via leads or wires and controls the time interval during which the solenoid valve is to be opened. It is the output of the electronic timing circuit (5) that activates the solenoid valve. When the output is off, the valve is closed. When the output is on, the solenoid valve is open and the calibration gas that is supplied from the calibration gas source flows through the regulator (1) and into and through the solenoid valve (4). Once the calibration gas flows though the solenoid valve, it then exits and passes through the barb exit (18) of the barb (16) (when present) and flows into the instrument to be calibrated. The time interval for the electronic timing circuit (5) can be set to have a broad range of times dependent upon the needs of the customer. In most instances, the timing interval will vary from as little as about one millisecond to about eight minutes. In a preferred embodiment, the time interval will vary from about one millisecond to about five minutes, more preferably from about one second to about one minute and even more preferably from about one second to about seven seconds. This time, considered with the flow rate, determines the volume of calibration gas dispensed.

In one embodiment of the present invention, it is envisioned that the apparatus of the present invention will be provided such that the gas delivery device (2) has a preset time for gas flow which cannot be changed by the operator. In this embodiment, while not necessary, the gas delivery device (2) could also include a potentiometer (19) (that works in conjunction with the electronic timing circuit (5)) to preset the time. This potentiometer (19) would also be located inside of the case (3) of the gas delivery device (2). FIG. 9 demonstrates just such an embodiment which includes a preset time for gas flow.

In a still further embodiment of the present invention, the electronic timing circuit (5) includes a means for varying the time for gas flow into and through the solenoid valve (4). In this embodiment, the means for varying the time for gas flow comprises a potentiometer (19) connected to a means to adjust the potentiometer (20). In the present embodiment, the potentiometer (19) would be positioned inside of the case (3) of the gas delivery device (2). The means to adjust the potentiometer (20) can be located either inside the case (3) (in which situation the operator would have to open the case (3) to adjust the gas flow time or insert a device such as a screw driver to adjust the gas flow time) or could extend from the inside of the case (3) to the outside of the case (3) (in which situation the operator would be able to readily adjust the gas flow time without having to open the case (3)). The means for adjusting the potentiometer (20) (selecting the desired timing and consequently volumes of gas) may be any means that is readily known in the art, including but not limited to, a knob positioned on the inside or outside of the case (3) (as depicted in FIGS. 1 to 8) which includes pre-designated settings, a switch which can be flipped to one of several pre-designated settings also located on the inside or outside of the case (3) and finally, a dial also located on the inside or outside of the case (3) which could be moved to a designated gas flow and locked into place. Further reference is made to FIG. 8 of the present invention which provides for an even further embodiment in which the means to adjust the potentiometer (20) is located on one end of the exterior of the cylindrical case (3) and comprises an adjustable knob (21) seated in the case enclosure top (3.3) and having a numerical scale (23) that corresponds to the time that the gas is to be dispensed optionally overlaid with a clear covering (22) positioned between the adjustable knob (21) and the case top (3.2). This allows for selection of the designated amount to be dispenses by rotating the adjustable knob (21) to the corresponding designation on the scale (23) which can be viewed through the clear covering (22). The operator has the option of ordering the metered flow apparatus with a preset time or with the option of setting the time in the field.

The present apparatus also comprises a means for providing power (6) to the solenoid valve (4) and the electronic timing circuit (5). In a preferred embodiment, the means for providing power (6) comprises either one or more batteries (6) or an external power source (6). When the means for providing power (6) comprises one or more batteries, the one or more batteries are preferably enclosed in the case (3) with the solenoid valve (4) and the electronic timing circuit (5). FIGS. 1 and 9 depict embodiments with one battery while FIG. 5 depicts an embodiment with more than one battery. However, it is not necessary for the one or more batteries to be in the case (3). Therefore, the present invention further provides an additional embodiment in which the one or more batteries are positioned on the outside of the case (3) (not shown). When the one or more batteries are positioned on the outside of the case (3), they will preferably be attached to the case (3) in some manner such as by a holder which will provide for the power generated by the one or more batteries to pass from the batteries, through the case (3) and to be supplied to the solenoid valve (4) and electronic timing circuit (5).

Any type of batteries may be utilized as a power source for the apparatus of the present invention. For example, the batteries may be standard batteries or rechargeable batteries. In a preferred embodiment of the present invention, the power source (6) comprises rechargeable batteries. When rechargeable batteries are utilized, for the ease of recharging the batteries, the present invention may also include a power port (24) as shown in FIGS. 5 and 6 which will accept the plug of a battery recharger. (In an alternative embodiment, the external source of power will provide connection through this port (24)). This would allow battery recharging by means of any additional power source including but not limited to a power outlet or a DC outlet located in a car or other power source.

In a further embodiment of the present invention, the means for providing power (6) comprises an external power source selected from a power supply or USB connection. This means for providing power (6) would allow for the connection of the external source to the electronic timing circuit (5) and solenoid valve (4) via a power port (24) that is located in the case (3). In a still further embodiment of the present invention, the means for providing power (6) to the solenoid valve (4) and the electronic timing circuit (5) comprises a means to accept electronic signals from the attached gas monitoring instrument to be calibrated.

The gas delivery device (2) also contains a power switch (7) for activating the electronic timing circuit (5). The power switch (7) may be in the form of a knob, a button, a flip switch, or any other means which allows for the device to be turned off and on. While the power switch (7) may be located anywhere on the gas delivery device (2), including inside of the case (3), in the most preferred embodiment the power switch (7) is located on the front of the case (3) as shown in FIG. 3. However, the location of the power switch (7) is not critical to the invention. The only requirement is that the power switch (7) be located in a convenient place that is accessible by the operator utilizing the portable device.

The gas delivery device (2) of the metered flow apparatus also comprises a means for activating the release of calibration gas (8). This means, once triggered, communicates to the electronic timing device the need to activate the output and consequently open the solenoid valve. In one embodiment, the means for activating the releases of calibration gas (8) comprises a pushbutton switch. The pushbutton switch is placed in such a manner as to allow the operator to activate the flow of calibration gas to the instrument to be calibrated with one hand. This is further shown in FIGS. 3 and 6. In a still further embodiment of the present invention, the power switch (7) is located at one end of the metered flow apparatus along with the means for activating the release of calibration gas (8) as shown in FIG. 9. This allows for pushbutton switches to be utilized and for the apparatus to be operated using a finger or thumb to activate both switches.

In addition to the pushbutton switch, the present apparatus is made easier to use by the addition of one or more light emitting diodes (LED) (depicted as 25 and 26 in the various embodiments set forth in the FIGS. 1, 3 to 9). In one embodiment, the apparatus comprises a first LED light (25) that illuminates green (or any other color) when the metered flow apparatus is ready for operation and turns off or blinks during gas flow (dispensing of calibration gas). The metered flow apparatus may also include an optional second LED light (26) that illuminates red (or any other color) and lights up when the batteries are depleted below a minimal threshold (are getting close to losing their charge) thereby notifying the operator that the one or more batteries should be replaced (as in the case of standard batteries) or recharged (as in the case of rechargeable batteries). In a further embodiment represented by FIGS. 5 and 6, the power switch (7) is combined with the first LED light (25). The LED lights are controlled through the timing circuit. In order to easily identify the various components (LED lights, buttons, knobs and switches) it is also possible to include a face (28) on the surface of the case (3) which will identify the various components represented by the LED lights, buttons, knobs and switches.

The present invention further comprises a calibration system that includes the metered flow apparatus of the present invention as described hereinbefore and a portable calibration gas source in the form of a gas cylinder or a vessel as described hereinbefore. Such systems are readily portable and can be carried in the field.

The metered flow apparatus of the present invention accurately provides calibration gas from a calibration gas source to a gas monitoring instrument in order to permit calibration or bump testing of that instrument. One of the key aspects of the present invention is the ability of the user to operate the invention with ease while maintaining an accurate release of gas in each instance. Based on the design of the metered flow apparatus, it is simple to use. The operator simply turns on the power to the unit (typically by pushing a power switch (7)) thereby supplying power to the electronic timing circuit (5) and the solenoid valve (4). Once the power switch (7) has been activated to turn on the electronic timing circuit (5), the first LED light (25) will be illuminated green to indicate the unit is ready for operation. Note that in FIG. 5, the power switch and the first LED light (25) are the same therefore, when the power switch is activated, the power switch will turn green when ready. In models that include a selection of dispensing volumes/times, the operator will then adjust for the desired time (and consequently volume) that gas is to be dispensed. Next the operator presses the means for activating the release of calibration gas (8). At this time the LED light (green in this embodiment) will turn off or preferably blink thereby indicating that the solenoid valve has opened, and the calibration gas is being released from the cylinder (calibration gas source) and is passing through the regulator (1) and solenoid valve (4) into the instrument to be calibrated/bump tested. Based on the pre-selected setting with regard to the time (in some instances there is a means of adjustment which will allow an operator to select from a variety of times while in other instances the time is preset at the factory and cannot be changed by the operator), the electronic timing circuit (5) holds the valve open until the specified time has passed. After the specified time has passed, the electronic timing circuit (5) signals the solenoid valve to close, the gas flow ceases and the first LED (25) green light turns back on or becomes steady (no longer blinks). Once this occurs, the power switch (7) can be turned off and the reading for the instrument to be calibrated taken.

The present metered flow apparatus can be used in a variety of fields including the industrial hygiene field for calibrating gas monitoring devices which are used to monitor or detect certain toxic or hazardous gases in an environment (such as a confined area such as a mine) as well as in the field of breath analyzing where breathalyzer instruments are used to measure breath alcohol content.

Accordingly, the present invention further provides a method for calibration/bump testing of an industrial hygiene gas monitoring device or a breath alcohol gas monitoring device utilizing the metered flow apparatus of the present invention that comprises a regulator in combination with a gas delivery device as described hereinbefore. The method comprises first attaching the regulator of the portable metered flow apparatus as described hereinbefore to the outlet of a cylinder of a source of calibration gas to form a calibration system. In the next step, the calibration system is attached to the gas monitoring device to be calibration/bump tested via the outlet of the gas delivery device. Once this connection is secured, the power switch is turned on so that the power source will supply the needed power to the electronic timing circuit and solenoid valve. After the power switch is turned on, the LED will illuminate green to indicate that the calibration system is functioning and ready. In those devices where there is the ability to adjust the amount/timing of dispensing of the calibration gas (those systems which are not preset for amount/timing), the means for adjusting the potentiometer is adjusted to allow the operator to choose the timing/amount of gas to be dispensed. Once this choice has been made (in those systems where the option is present), the means for the release of calibration gas is activated thereby allowing the opening of the solenoid valve in the solenoid valve, and consequently, the flow of gas from the calibration gas source, through the regulator where the pressure is adjusted and into the solenoid valve, where the correct amount of gas passes through the solenoid valve and into the machine to be calibrated. As the calibration gas begins to make this passage, the first LED light will begin to blink and will continue to blink as long as the gas flows. Once the appropriate amount of calibration gas has flowed through the solenoid valve and into the instrument to be calibrated, the valve automatically closes thereby terminating the flow of calibration gas. At this point, the LED light will return to a solid color (will cease to blink) and thereby signal the operator that the gas has been dispensed and the power switch can be turned off. Once the power switch is turned off, the reading is taken for the unit being calibration/bump tested.

It will be understood that many additional changes in the details, materials, steps and arrangement of parts, which have been herein described in order to explain the nature of the invention, may be made by those skilled in the art within the principle and scope of the invention as expressed in the appended claims. Thus, the present invention is not intended to be limited to the specific embodiments in the examples given above.

What is claimed is:

1. A portable metered flow apparatus for accurately providing gas from a gas source, the apparatus comprising:
    a) a regulator having two opposing ends, a passageway that extends through the regulator between the two opposing ends, the first end of the regulator including a regulator inlet and the opposing end of the regulator including a regulator outlet, and a pressure regulator located in the passageway between the regulator inlet and the regulator outlet, the regulator inlet configured to be capable of being connected to the gas source and form a connection adapted to allow passage of the gas into the regulator,
    b) a gas delivery device comprising a hollow case having a case inlet and a case outlet and having disposed within said case:
        A) a valve having an entrance for the gas and an exit for the gas, the entrance for the gas configured to connect the valve to the regulator outlet, the valve adapted to be capable of allowing passage of gas through the valve when the valve is in an opened configuration;

B) an electronic timing circuit operably connected to the valve and configured to open and close the valve, the electronic timing circuit configured to open the valve for a time interval and then close the valve after the time interval, wherein the electronic timing circuit is enclosed within the hollow case;

C) a power delivery element adapted to power the portable metered flow apparatus, D) a power switch configured to be capable of activating the portable metered flow apparatus;

E) an activation trigger adapted to release the gas from the regulator,

F) a first light adapted to illuminate when the apparatus is ready for operation and blink when the calibration gas is being dispensed; and G) a second light adapted to illuminate when the power delivery element needs to be replaced or recharged, wherein the gas delivery device is in the shape of a cylinder and the power switch, first light, second light and activation trigger are all disposed at the end of the cylinder opposite the end adapted to be connected to the regulator.

2. A portable metered flow apparatus for accurately providing gas from a gas source, the apparatus comprising:

a) a regulator having two opposing ends, a passageway that extends through the regulator between the two opposing ends, the first end of the regulator including a regulator inlet and the opposing end of the regulator including a regulator outlet, and a pressure regulator located in the passageway between the regulator inlet and the regulator outlet, the regulator inlet configured to be capable of being connected to the gas source and form a connection adapted to allow passage of the gas into the regulator, b) a gas delivery device comprising a hollow case having a case inlet and a case outlet and having disposed within said case:

A) a valve having an entrance for the gas and an exit for the gas, the entrance for the gas configured to connect the valve to the regulator outlet, the valve adapted to be capable of allowing passage of gas through the valve when the valve is in an opened configuration;

B) an electronic timing circuit operably connected to the valve and configured to open and close the valve, the electronic timing circuit configured to open the valve for a time interval and then close the valve after the time interval, wherein the electronic timing circuit is enclosed within the hollow case, C) a power delivery element adapted to power the portable metered flow apparatus, D) a power switch configured to be capable of activating the portable metered flow apparatus; and E) an activation trigger adapted to release the gas from the regulator, wherein the electronic timing circuit comprises a potentiometer and a potentiometer adjustment element.

3. A portable metered flow apparatus for accurately providing gas from a gas source, the apparatus comprising:

a) a regulator having two opposing ends, a passageway that extends through the regulator between the two opposing ends, the first end of the regulator including a regulator inlet and the opposing end of the regulator including a regulator outlet, and a pressure regulator located in the passageway between the regulator inlet and the regulator outlet, the regulator inlet configured to be capable of being connected to the gas source and form a connection adapted to allow passage of the gas into the regulator, b) a gas delivery device comprising a hollow case having a case inlet and a case outlet and having disposed within said case:

A) a valve having an entrance for the gas and an exit for the gas, the entrance for the gas configured to connect the valve to the regulator outlet, the valve adapted to be capable of allowing passage of gas through the valve when the valve is in an opened configuration;

B) an electronic timing circuit operably connected to the valve and configured to open and close the valve, the electronic timing circuit configured to open the valve for a time interval and then close the valve after the time interval, wherein the electronic timing circuit is enclosed within the hollow case.

4. The portable metered flow apparatus of claim 3, further comprising a power delivery element adapted to power the portable metered flow apparatus.

5. The portable metered flow apparatus of claim 4, wherein the power delivery element is one or more of a standard battery, a rechargeable battery, a plug adapted to operably connect to an external power supply, or a USB connection.

6. The portable metered flow apparatus of claim 3, further comprising a power switch configured to be capable of activating the portable metered flow apparatus.

7. The portable metered flow apparatus of claim 3, further comprising an activation trigger adapted to release the gas from the regulator.

8. The portable metered flow apparatus of claim 3, wherein the timing interval is from one millisecond to seven seconds.

9. The portable metered flow apparatus of claim 3, wherein the timing interval is from one millisecond to eight minutes.

10. The portable metered flow apparatus of claim 3, wherein the timing interval is a preset time.

11. The portable metered flow apparatus of claim 3, wherein the time interval consists of a fixed amount of time.

12. The portable metered flow apparatus of claim 3, further comprising a time interval adjustment element adapted to change the time interval.

13. The portable metered flow apparatus of claim 12, wherein the electronic timing circuit comprises a potentiometer and wherein the time interval adjustment element is adapted to adjust the potentiometer.

14. The portable metered flow apparatus of claim 3, further comprising a power delivery element adapted to power the portable metered flow apparatus, a power switch configured to be capable of activating the portable metered flow apparatus and an activation trigger adapted to release the gas from the regulator, wherein the time interval consists of a fixed and preset amount of time.

15. A process for calibration/bump testing of a gas monitoring device comprising the steps of:

a) forming a calibration system by attaching a cylinder of calibration gas to a portable metered flow apparatus of claim 1, b) further attaching the calibration system to the gas monitoring device to be calibrated/bump tested;

c) activating the power switch in order to supply power to the electronic timing circuit and solenoid valve and illuminate the first light thereby indicating the calibration system is functioning and ready;

d) activating the activation trigger which causes the electronic timing circuit to open the valve and consequently allow the flow of gas from a calibration gas cylinder through the regulator where the pressure is adjusted and into the valve where the correct amount of calibration gas is allowed to pass through the valve and into the machine to be calibrated during which time the first light will blink to indicate that a calibration gas is flowing;

e) turning the power switch off once the appropriate amount of calibration gas has flowed into the instrument to be calibrated, as evidenced by the valve automatically closing and the light ceasing to blink;

f) taking a reading of the instrument being calibrated; and g) wherein the cylinder of calibration gas comprises a non-refillable gas cylinder.

16. The process of claim 15 wherein the gas monitoring instrument is a breathalyzer instrument adapted to measure a breath alcohol content.

17. The process of claim 15 wherein the gas monitoring instrument is an instrument adapted to monitor or detect toxic or hazardous gases.

* * * * *